US011891665B2

(12) United States Patent
Grant et al.

(10) Patent No.: US 11,891,665 B2
(45) Date of Patent: Feb. 6, 2024

(54) COMPOSITIONS FOR DIFFERENTIATING LATENT AUTOIMMUNE DIABETES IN ADULTS FROM CHILDHOOD-ONSET TYPE 1 DIABETES AND METHODS FOR DIAGNOSING AND TREATING DISEASE

(71) Applicant: The Children's Hospital of Philadelphia, Philadelphia, PA (US)

(72) Inventors: Struan Frederick Grant, Swarthmore, PA (US); Rajashree Mishra, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 145 days.

(21) Appl. No.: 16/616,122

(22) PCT Filed: May 25, 2018

(86) PCT No.: PCT/US2018/034666
§ 371 (c)(1),
(2) Date: Nov. 22, 2019

(87) PCT Pub. No.: WO2018/218156
PCT Pub. Date: Nov. 29, 2018

(65) Prior Publication Data
US 2020/0123611 A1    Apr. 23, 2020

Related U.S. Application Data

(60) Provisional application No. 62/510,926, filed on May 25, 2017.

(51) Int. Cl.
    C12Q 1/6883    (2018.01)
    C12Q 1/6881    (2018.01)
    G01N 33/564    (2006.01)
    G01N 33/74     (2006.01)

(52) U.S. Cl.
    CPC ......... *C12Q 1/6883* (2013.01); *C12Q 1/6881* (2013.01); *G01N 33/564* (2013.01); *G01N 33/74* (2013.01); *C12Q 2600/112* (2013.01); *C12Q 2600/156* (2013.01); *C12Q 2600/172* (2013.01); *G01N 2800/042* (2013.01); *G01N 2800/50* (2013.01); *G01N 2800/60* (2013.01)

(58) Field of Classification Search
    CPC ................. C12Q 1/6883; C12Q 2600/156
    See application file for complete search history.

(56) References Cited

PUBLICATIONS

Baschal (Diabelologia (2011) vol. 54, pp. 1702-1709).*
Noble, J.A. et al. Diabetes 59:2972. (Year: 2010).*
Noble, J.A. et al. Curr. Diab. Rep. 11:533. (Year: 2011).*
Culina, S. et al. European Journal of Endocrinology 168:R19. (Year: 2013).*
Andersen, Metgte K. et al., "Type 2 diabetes susceptibility gene variants predispose to adult-onset autoimmune diabetes", Diabetologia, 57: 1859-1868 (2014).

(Continued)

*Primary Examiner* — Diana B Johannsen
(74) *Attorney, Agent, or Firm* — Kathleen D. Rigaut; Howson & Howson LLP

(57) ABSTRACT

Compositions for the identification of patients at risk for the development of latent autoimmune diabetes, and methods of use thereof, for the diagnosis and treatment of the same.

6 Claims, 8 Drawing Sheets

Specification includes a Sequence Listing.

(56) References Cited

PUBLICATIONS

Baschal, E.E. et al., "The HLA-B*3906 allele imparts a high risk of diabetes only on specific HLA-DR/DQ haplotypes", Diabetologia, 54: 1702-1709 (2011).

Bradfield, Jonathan P. et al., "A Genome-Wide Meta-Analysis of Six Type 1 Diabetes Cohorts Identifies Multiple Associated Loci", PLoS Genetics, 7(9): e1002293 (2011).

Cervin, Camilla et al., "Genetic Similarities Between Latent Autoimmune Diabetes in Adults, Type 1 Diabetes, and Type 2 Diabetes", Diabetes, 57: 1433-1437 (2008).

Desai, Minal et al., "The Variable Number of Tandem Repeats Upstream of the Insulin Gene is a Susceptibility Locus for Latent Autoimmune Diabetes in Adults", 55: 1890-1894 (2006).

Desai, M. et al., "An association analysis of the HLA gene region in latent autoimmune diabetes in adults", Diabetologia, 50(1): 68-73 (2007).

Hawa, Mohammed I. et al., "Adult-Onset Autoimmune Diabetes in Europe is Prevalent with a Broad Clinical Phenotype", Diabetes Care, 36: 908-913 (2013).

Horton, V. et al., "Genetic heterogeneity of autoimmune diabetes: age of presentation in adults is influenced by HLA DRB21 and DQB1 genotypes (UKPDS 43)", Diabetologia, 42: 608-616 (1999).

Kisand, K. et al., "LADA and T1D in Estonian population—two different genetic risk profiles", Gene, 497(2): 285-91 (2012).

Lukacs, K. et al., "The type 2 diabetes-associated variant in TCF7L2 is associated with latent autoimmune diabetes in adult Europeans and the gene effect is modified by obesity: a meta-analysis and an individual study", Diabetologia, 55: 68-693 (2012).

Luo, Shuoming et al., "HLA Genetic Discrepancy Between Latent Autoimmune Diabetes in Adults and Type 1 Diabetes: LADA China Study No. 6", J. Clin. Endocrinol. Metab. 101(4): 1693-1700 (2016).

Maddaloni, Ernesto et al., "Latent Autoimmune Diabetes in Adults in the United Arab Emirates: Clinical Features and Factors Related to Insulin-Requirement", PLoS One, 10(8): e0131837 (2015).

Mahajan, A., "Genome wide trans-ancestry meta-analysis provides insight into the genetic architecture of type 2 diabetes susceptibility", Nat. Genet., 46(3): 234-244 (2014).

Mishra, Rajashree et al., "Relative contribution of type 1 and type 2 diabetes loci to the genetic etiology of adult-onset, non-insulin-requiring autoimmune diabetes", BMC Medicine, 15:88 (2017).

Oram, Richard A. et al., "A Type 1 Diabetes Genetic Risk Score Can Aid Discrimination BEeween Type 1 and Type 2 Diabetes in Young Adults", Diabetes Care, 39: 337-344 (2016).

Todd, John A. et al., "HLA-DQB gene contributes to susceptibility and resistance to insulin-dependent diabetes mellitus", Nature, 329: 599-604 (1987).

Tuomi, T. et al., "Clinical and Genetic Characteristics of Type 2 Diabetes With and Without GAD Antibodies", Diabetes, 48: 150-157 (1999).

Tuomi, Tiinamaija et al., "Antibodies to Glutamic Acid Decarboxylase Reveal Latent Autoimmune Diabetes Mellitus in Adults with a Non-Insulin-Dependent Onset of Disease", Diabetes, 42: 359-62 (1993).

Weber, P., "Type 1 diabetes and LADA-occurrence of HLA-DRB1 *03 and DRB1 *04 alleles in two age different groups of diabetics", Adv. Gerontol., 23(2): 243-8 (2010) [Abstract only].

Zampetti, S. et al., "Association of TCF7L2 gene variants with low GAD autoantibody titre in LADA subjects (NIRAD Study 5)", Diabetic Medicine, 27: 701-704 (2010).

Zhou, Zhiguang et al., "Frequency, Immunogenetics, and Clinical Characteristics of Latent Autoimmune Diabetes in China (LADA China Study)", Diabetes, 62: 543-550 (2013).

International Search Report and Written Opinion, dated Sep. 20, 2018, issued in corresponding International Application No. PCT/US18/34666, filed May 25, 2018.

* cited by examiner

Fig. 3A
HLA-DQB1*03:02 and HLA-DQB1*02:01 (4 DIGIT ALLELE)
The base sequence is the HLA-DQB1*02:01 sequence reported in the
FASTQ file. There are 3510 versions of HLA-DQB1*03 and 624
versions on HLA-DRB1*03:02. There are 936 versions of HLA-
DQB1*03 and 78 versions on HLA-DRB1*03:02. To see the exact
changes for each allele, you would have to use the following
reference:

available on the world wide web at: raw.githubusercontent.com/ANHIG/
IMGTHLA/Latest/alignment s/DQB1 gen.txt HLA-DRB1*15:01 (4 DIGIT ALLELE)
The base sequence is the sequence reported in the FASTQ file.
There are 211 versions of HLA-DRB1*15 and 36 versions on HLA-
DRB1*15:01. To see the exact changes for each allele, you would
have to use the following reference:

available on the world wide web at: raw.githubusercontent.com/ANHIG/
IMGTHLA/Latest/alignment s/DRB1 gen.txt HLA-B*39:06 (4 DIGIT ALLELE)
The reference sequence is the sequence for B*07:02:01:01. There
are 1638 versions of HLA-B*39 and 168 versions on HLA-B*39:06.
To see the exact changes for each allele, you would have to use
the following reference:

available on the world wide web at: raw.githubusercontent.com/ANHIG/
IMGTHLA/Latest/alignment s/B gen.txt HLA-A*11 (2 DIGIT ALLELE)
The reference sequence is the sequence for A*01:01:01:01. There are
67 versions of HLA-A*11. To see the exact changes for each
allele, you would have to use the following reference:

available on the world wide web at: raw.githubusercontent.com/ANHIG/
IMGTHLA/Latest/alignment s/A gen.txt

Fig. 3B

The following convention in order to understand the file format:
- The entry for each allele is displayed in respect to the
    reference sequences.
- Where identity to the reference sequence is present the base
    will be displayed as a hyphen (-).
- Non-identity to the reference sequence is shown by displaying
    the appropriate base at that position.
- Where an insertion or deletion has occurred this will be
    represented by a period (.).
- If the sequence is unknown at any point in the alignment, this
    will be represented by an asterisk (*).
- In protein alignments for null alleles, the 'Stop' codons will
    be represented by a capital X.
- In protein alignments, sequence following the termination
    codon, will not be marked and will appear blank.

*These conventions are used for both nucleotide and protein
alignments.

>HLA:HLA00622 DQB1*02:01:01 786 bp
ATGTCTTGGAAAAAGGCTTTGCGGATCCCCGGAGGCCTTCGGGCAGCAACTGTGACCTTG
ATGCTGTCGATGCTGAGCACCCCAGTGGCTGAGGGCAGAGACTCTCCCGAGGATTTCGTG
TACCAGTTTAAGGGCATGTGCTACTTCACCAACGGGACAGAGCGCGTGCGTCTTGTGAGC
AGAAGCATCTATAACCGAGAAGAGATCGTGCGCTTCGACAGCGACGTGGGGGAGTTCCGG
GCGGTGACGCTGCTGGGGCTGCCTGCCGCCGAGTACTGGAACAGCCAGAAGGACATCCTG
GAGAGGAAACGGGCGGCGGTGGACAGGGTGTGCAGACACAACTACCAGTTGGAGCTCCGC
ACGACCTTGCAGCGGCGAGTGGAGCCCACAGTGACCATCTCCCCATCCAGGACAGAGGCC
CTCAACCACCACAACCTGCTGGTCTGCTCGGTGACAGATTTCTATCCAGCCCAGATCAAA
GTCCGGTGGTTTCGGAATGACCAGGAGGAGACAGCTGGCGTTGTGTCCACCCCCCTTATT
AGGAATGGTGACTGGACCTTCCAGATCCTGGTGATGCTGGAAATGACTCCCCAGCGTGGA
GACGTCTACACCTGCCACGTGGAGCACCCCAGCCTCCAGAGCCCCATCACCGTGGAGTGG
CGGGCTCAATCTGAATCTGCCCAGAGCAAGATGCTGAGTGGCATTGGAGGCTTCGTGCTG
GGGCTGATCTTCCTCGGGCTGGGCCTTATCATCCATCACAGGAGTCAGAAGGGCTCCTG
CACTGA

Fig. 3C

>HLA:HLA00627 DQB1*03:02:01:01 786 bp
ATGTCTTGGAAGAAGGCTTTGCGGATCCCTGGAGGCCTTCGGGTAGCAACTGTGACCTTG
ATGCTGGCGATGCTGAGCACCCCGGTGGCTGAGGGCAGAGACTCTCCCGAGGATTTCGTG
TACCAGTTTAAGGGCATGTGCTACTTCACCAACGGGACGGAGCGCGTGCGTCTTGTGACC
AGATACATCTATAACCGAGAGGAGTACGCACGCTTCGACAGCGACGTGGGGGTGTATCGG
GCGGTGACGCCGCTGGGGCCGCCTGCCGCCGAGTACTGGAACAGCCAGAAGGAAGTCCTG
GAGAGGACCCGGGCGGAGTTGGACACGGTGTGCAGACACAACTACCAGTTGGAGCTCCGC
ACGACCTTGCAGCGGCGAGTGGAGCCCACAGTGACCATCTCCCCATCCAGGACAGAGGCC
CTCAACCACCACAACCTGCTGGTCTGCTCAGTGACAGATTTCTATCCAGCCCAGATCAAA
GTCCGGTGGTTTCGGAATGACCAGGAGGAGACAACTGGCGTTGTGTCCACCCCCTTATT
AGGAACGGTGACTGGACCTTCCAGATCCTGGTGATGCTGGAAATGACTCCCCAGCGTGGA
GACGTCTACACCTGCCACGTGGAGCACCCCAGCCTCCAGAACCCCATCATCGTGGAGTGG
CGGGCTCAGTCTGAATCTGCCCAGAGCAAGATGCTGAGTGGCATTGGAGGCTTCGTGCTG
GGGCTGATCTTCCTCGGGCTGGGCCTTATTATCCATCACAGGAGTCAGAAAGGGCTCCTG
CACTGA

>HLA:HLA00865 DRB1*15:01:01:01 801 bp
ATGGTGTGTCTGAAGCTCCCTGGAGGCTCCTGCATGACAGCGCTGACAGTGACACTGATG
GTGCTGAGCTCCCCACTGGCTTTGTCTGGGGACACCCGACCACGTTTCCTGTGGCAGCCT
AAGAGGGAGTGTCATTTCTTCAATGGGACGGAGCGGGTGCGGTTCCTGGACAGATACTTC
TATAACCAGGAGGAGTCCGTGCGCTTCGACAGCGACGTGGGGGAGTTCCGGGCGGTGACG
GAGCTGGGGCGGCCTGACGCTGAGTACTGGAACAGCCAGAAGGACATCCTGGAGCAGGCG
CGGGCCGCGGTGGACACCTACTGCAGACACAACTACGGGGTTGTGGAGAGCTTCACAGTG
CAGCGGCGAGTCCAACCTAAGGTGACTGTATATCCTTCAAAGACCCAGCCCCTGCAGCAC
CACAACCTCCTGGTCTGCTCTGTGAGTGGTTTCTATCCAGGCAGCATTGAAGTCAGGTGG
TTCCTGAACGGCCAGGAAGAGAAGGCTGGGATGGTGTCCACAGGCCTGATCCAGAATGGA
GACTGGACCTTCCAGACCCTGGTGATGCTGGAAACAGTTCCTCGAAGTGGAGAGGTTTAC
ACCTGCCAAGTGGAGCACCCAAGCGTGACAAGCCCTCTCACAGTGGAATGGAGAGCACGG
TCTGAATCTGCACAGAGCAAGATGCTGAGTGGAGTCGGGGGCTTTGTGCTGGGCCTGCTC
TTCCTTGGGGCCGGGCTGTTCATCTACTTCAGGAATCAGAAAGGACACTCTGGACTTCAG
CCAACAGGATTCCTGAGCTGA

Fig. 3D
>HLA:HLA00279 B*39:06:01 1089 bp
ATGCTGGTCATGGCGCCCCGAACCGTCCTCCTGCTGCTCTCGGCGGCCCTGGCCCTGACC
GAGACCTGGGCCGGCTCCCACTCCATGAGGTATTTCTACACCTCCGTGTCCCGGCCCGGC
CGCGGGGAGCCCCGCTTCATCTCAGTGGGCTACGTGGACGACACGCAGTTCGTGAGGTTC
GACAGCGACGCCGCGAGTCCGAGAGAGGAGCCGCGGGCGCCGTGGATAGAGCAGGAGGGG
CCGGAATATTGGGACCGGAACACACAGATCTGCAAGACCAACACACAGACTGACCGAGAG
AGCCTGCGGAACCTGCGCGGCTACTACAACCAGAGCGAGGCCGGGTCTCACACTTGGCAG
ACGATGTACGGCTGCGACGTGGGGCCGGACGGGCGCCTCCTCCGCGGGCATAACCAGTTC
GCCTACGACGGCAAGGATTACATCGCCCTGAACGAGGACCTGAGCTCCTGGACCGCGGCG
GACACCGCGGCTCAGATCACCCAGCGCAAGTGGGAGGCGGCCCGTGTGGCGGAGCAGCTG
AGAACCTACCTGGAGGGCACGTGCGTGGAGTGGCTCCGCAGATACCTGGAGAACGGGAAG
GAGACGCTGCAGCGCGCGGACCCCCCAAAGACACATGTGACCCACCACCCCATCTCTGAC
CATGAGGCCACCCTGAGGTGCTGGGCCCTGGGCTTCTACCCTGCGGAGATCACACTGACC
TGGCAGCGGGATGGCGAGGACCAAACTCAGGACACCGAGCTTGTGGAGACCAGACCAGCA
GGAGACAGAACCTTCCAGAAGTGGGCAGCTGTGGTGGTGCCTTCTGGAGAAGAGCAGAGA
TACACATGCCATGTACAGCATGAGGGCTGCCGAAGCCCCTCACCCTGAGATGGGAGCCA
TCTTCCCAGTCCACCGTCCCCATCGTGGGCATTGTTGCTGGCCTGGCTGTCCTAGCAGTT
GTGGTCATCGGAGCTGTGGTCGCTGCTGTGATGTGTAGGAGGAAGAGTTCAGGTGGAAAA
GGAGGGAGCTACTCTCAGGCTGCGTCCAGCGACAGTGCCCAGGGCTCTGATGTGTCTCTC
ACAGCTTGA

>HLA:HLA00043 A*11:01:01:01 1098 bp
ATGGCCGTCATGGCGCCCCGAACCCTCCTCCTGCTACTCTCGGGGGCCCTGGCCCTGACC
CAGACCTGGGCGGGCTCCCACTCCATGAGGTATTTCTACACCTCCGTGTCCCGGCCCGGC
CGCGGGGAGCCCCGCTTCATCGCCGTGGGCTACGTGGACGACACGCAGTTCGTGCGGTTC
GACAGCGACGCCGCGAGCCAGAGGATGGAGCCGCGGGCGCCGTGGATAGAGCAGGAGGGG
CCGGAGTATTGGGACCAGGAGACACGGAATGTGAAGGCCCAGTCACAGACTGACCGAGTG
GACCTGGGGACCCTGCGCGGCTACTACAACCAGAGCGAGGACGGTTCTCACACCATCCAG
ATAATGTATGGCTGCGACGTGGGGCCGGACGGGCGCTTCCTCCGCGGGTACCGGCAGGAC
GCCTACGACGGCAAGGATTACATCGCCCTGAACGAGGACCTGCGCTCTTGGACCGCGGCG
GACATGGCAGCTCAGATCACCAAGCGCAAGTGGGAGGCGGCCCATGCGGCGGAGCAGCAG
AGAGCCTACCTGGAGGGCCGGTGCGTGGAGTGGCTCCGCAGATACCTGGAGAACGGGAAG
GAGACGCTGCAGCGCACGGACCCCCCCAAGACACATATGACCCACCACCCCATCTCTGAC
CATGAGGCCACCCTGAGGTGCTGGGCCCTGGGCTTCTACCCTGCGGAGATCACACTGACC
TGGCAGCGGGATGGGGAGGACCAGACCCAGGACACGGAGCTCGTGGAGACCAGGCCTGCA
GGGGATGGAACCTTCCAGAAGTGGGCGGCTGTGGTGGTGCCTTCTGGAGAGGAGCAGAGA
TACACCTGCCATGTGCAGCATGAGGGTCTGCCCAAGCCCCTCACCCTGAGATGGGAGCTG
TCTTCCCAGCCCACCATCCCCATCGTGGGCATCATTGCTGGCCTGGTTCTCCTTGGAGCT
GTGATCACTGGAGCTGTGGTCGCTGCCGTGATGTGGAGGAGGAAGAGCTCAGATAGAAAA
GGAGGGAGTTACACTCAGGCTGCAAGCAGTGACAGTGCCCAGGGCTCTGATGTGTCTCTC
ACAGCTTGTAAAGTGTGA available on the world wide web at: hla.alleles.org/alleles/

COMPOSITIONS FOR DIFFERENTIATING LATENT AUTOIMMUNE DIABETES IN ADULTS FROM CHILDHOOD-ONSET TYPE 1 DIABETES AND METHODS FOR DIAGNOSING AND TREATING DISEASE

The present application is a § 371 of International Application No. PCT/US2018/034666, filed May 25, 2018, which claims benefit of U.S. Provisional Application No. 62/510,926 filed May 25, 2017, the entire contents being incorporated herein by reference as though set forth in full.

This invention was made with government support under R01 DK085212 awarded by the National Institutes of Health. The government has certain rights in the invention.

INCORPORATION-BY-REFERENCE OF MATERIAL SUBMITTED IN ELECTRONIC FORM

Incorporated herein by reference in its entirety is the Sequence Listing submitted via EFS-Web as a text file named SEQLIST.txt., created Sep. 28, 2021 and having a size of 7,069 bytes.

FIELD OF THE INVENTION

The present invention relates to the fields of autoimmune disease and diabetes in particular. More specifically, the invention provides compositions and methods useful for differentiating Type 1 diabetes (T1D) patients from latent autoimmune diabetes patients (LADA) to ascertain the appropriate treatment and screening protocols for such patients.

BACKGROUND OF THE INVENTION

Several publications and patent documents are cited throughout the specification in order to describe the state of the art to which this invention pertains. Each of these citations is incorporated herein by reference as though set forth in full.

Diabetes is a heterogeneous group of diseases resulting in hyperglycaemia due to insulin secretory dysfunction as well as insulin resistance. A substantial proportion of type 1 diabetes (T1D) cases present in adulthood, and despite the presence of diabetes-associated autoantibodies, the majority of these patients do not initially require insulin [1, 2]. The manifestation of this 'latent autoimmune diabetes in adulthood' (LADA) is clinically defined by (i) an adult age of onset, (ii) at least one diabetes-associated autoantibody, and (iii) the lack of requisite insulin treatment for at least 6 months after diagnosis. This definition overall represents ~5-10% of all cases of adult-onset diabetes, potentially the most frequent form of autoimmune diabetes [3, 4]. However, classifying adult-onset autoimmune T1D, including LADA, remains challenging. The need for insulin treatment is a clinical decision, while diabetes-associated autoantibodies are neither pathogenic nor categorical features of LADA. Decisions are further confounded by false positives when large numbers of patients are screened [5]. Since LADA has intermediate features between T1D and type 2 diabetes (T2D), there are limits to the current classification of diabetes. New paradigms are needed to distinguish LADA and ensure appropriate disease treatment and management.

SUMMARY OF THE INVENTION

In accordance with the present invention, a method for detecting a MHC HLA-B biomarker associated with altered risk of Type 1 Diabetes (T1D) and Latent autoimmune diabetes (LADA) is provided. An exemplary method entails providing a biological sample comprising nucleic acids obtained from a subject and genotyping the sample for MHC HLA haplotypes selected from HLA-DQB1*0302, HLA-DQB1*0201, HLA-DRB1*1501, HLA-B*3906 and HLA-A*11, the genotyping revealing the presence or absence of HLA-B*3906 and HLA-A*11, biomarkers for T1D, the absence of HLA-B*3906 and HLA-A*11 biomarker being indicative of an increased risk of LADA over T1D. In certain embodiments, the patient will not have been previously diagnosed with T1D or LADA. In other embodiments, the patient will present with diabetic symptoms.

Because LADA closely resembles T1D but develops in adulthood, once the subject has been identified as being at increased risk for LADA, the subject should be monitored periodically for development of autoimmune or diabetic symptoms. Accordingly, in another aspect of the invention, a method of monitoring a subject identified at increased risk of LADA identified by the aforementioned method is provided. An exemplary method comprises obtaining a biological sample from the subject and detecting in the sample one or more autoimmune disease and/or diabetes biomarkers and treating those patients having detectable autoimmune disease and/or diabetes biomarkers with anti-inflammatory or anti-diabetic agents in order to relieve symptoms associated with these disorders. Autoimmune biomarkers include autoantibodies such as Glutamic acid decarboxylase autoantibodies (GADA), Islet cell autoantibodies (ICA), IA-2-protein tyrosine phosphatase-like protein autoantibodies (IA-2A) Insulin autoantibodies (IAA), and Zinc transporter (ZnT8) autoantibodies. The patient can also be assessed for blood insulin, glucagon and sugar levels.

In yet another aspect of the invention, a method for confirming a diagnosis of LADA in a human subject previously diagnosed as having LADA by a physician is provided. This method comprise obtaining a nucleic acid sample from a subject suspected of having LADA and detecting whether the sample comprises MHC haplotypes HLA-DQB1*0302, HLA-DQB1*0201, HLA-DRB1*1501, HLA-B*3906 and HLA-A*11, by contacting the nucleic acid sample with a set of probes of sufficient length and composition to detect nucleic acids encoding said haplotypes, thereby confirming the diagnosis of LADA over T1D when haplotypes HLA-DQB1*0302, HLA-DQB1*0201, HLA-DRB1*1501 are present and haplotypes HLA-B*3906 and HLA-A*11 are absent.

In yet another aspect, the invention provides a kit for practicing the aforementioned methods.

BRIEF DESCRIPTION OF THE DRAWING

(FIG. 2C) Conditioning on top DRB1 and DQB1 signals. (FIG. 2D) conditions on top DRg1 and HLA-B signals.

FIGS. 3A-3D: Sequence information for the haplotypes which differentiate T1D from LADA. SEQ ID No: 1 is shown in FIG. 3B. SEQ ID Nos: 2-3 are shown in descending order in FIG. 3C. SEQ ID Nos: 4-5 are shown in descending order in FIG. 3D.

DETAILED DESCRIPTION OF THE INVENTION

Figure 1:
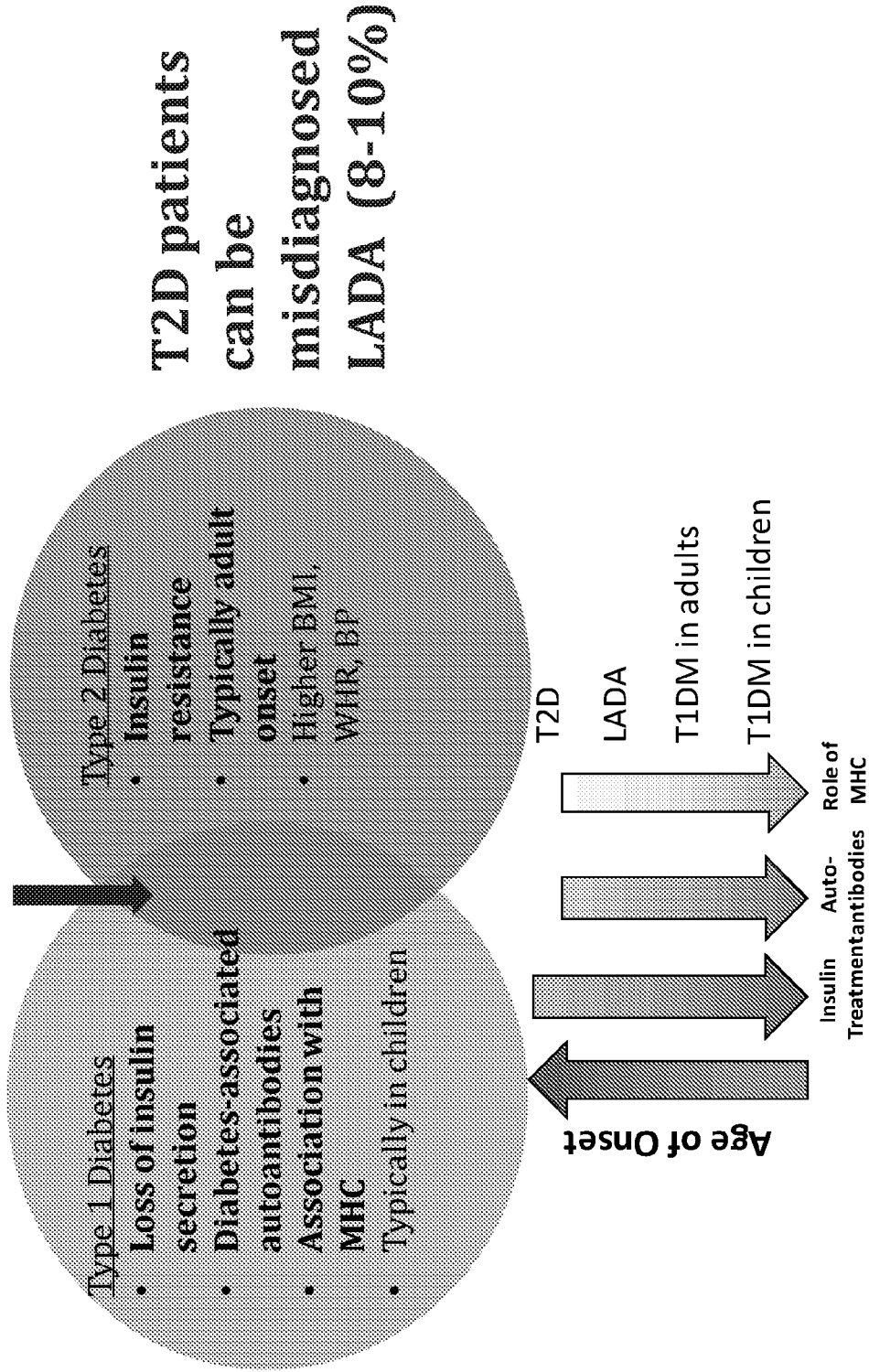
FIG. 1: A schematic diagram showing phenotypes associated with T1D, T2D and LADA.
Figures 2A, 2B:
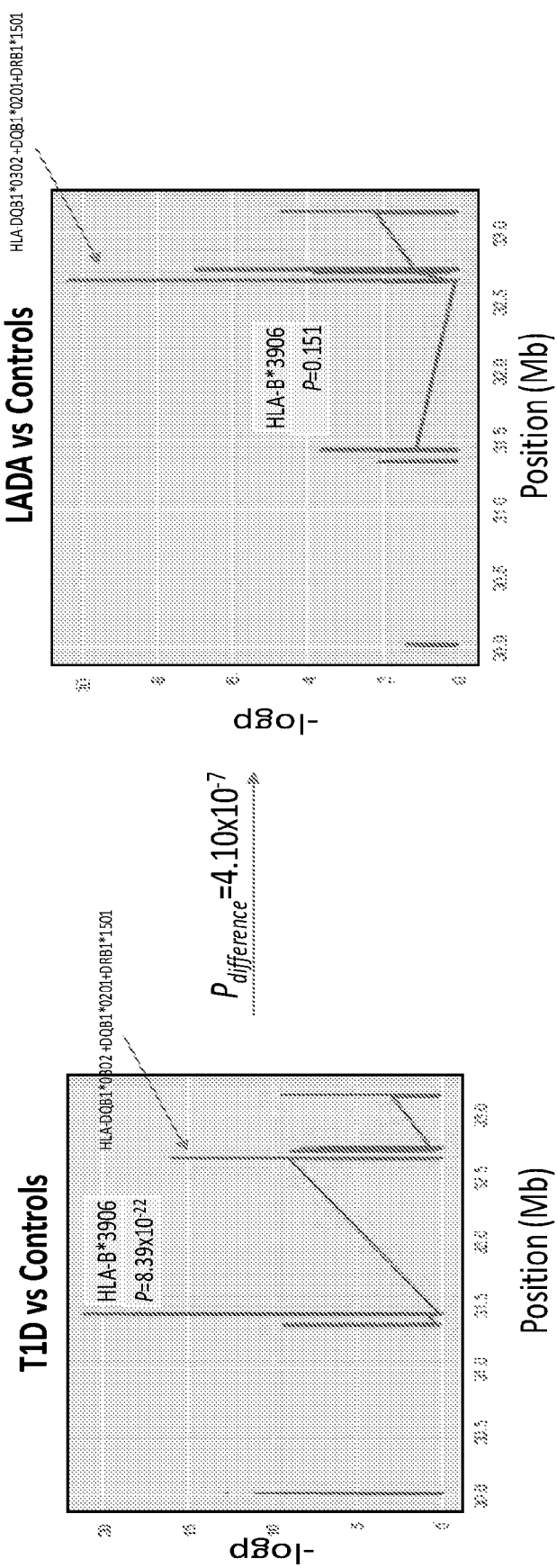
FIGS. 2A-2D: When conditioning on all three major haplotypes for both T1D and LADA, namely HLA-DQB1*0302, DQB1*0201 and DRB1*1501, a striking difference is observed. Conditioning within the T1D setting, reveals a highly significant association with HLA-B*3906, $P=8.39 \times 10^{-22}$ (FIG. 2A), while the same approach in LADA does not reveal association at all (P=0.151) (FIG. 2B). This marked difference is highly statistically significant, where the difference yields a $P=4.10 \times 10^{-7}$.
Figure 2C:
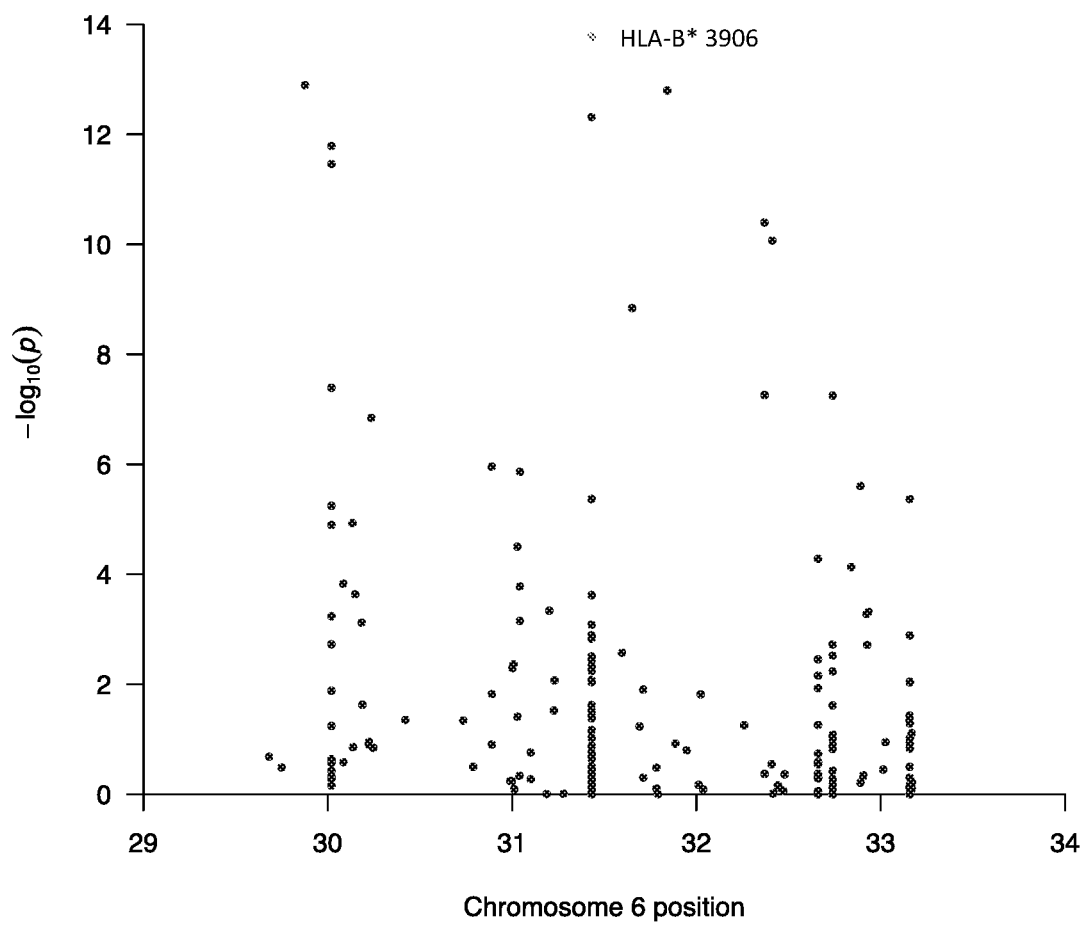
Figure 2D:
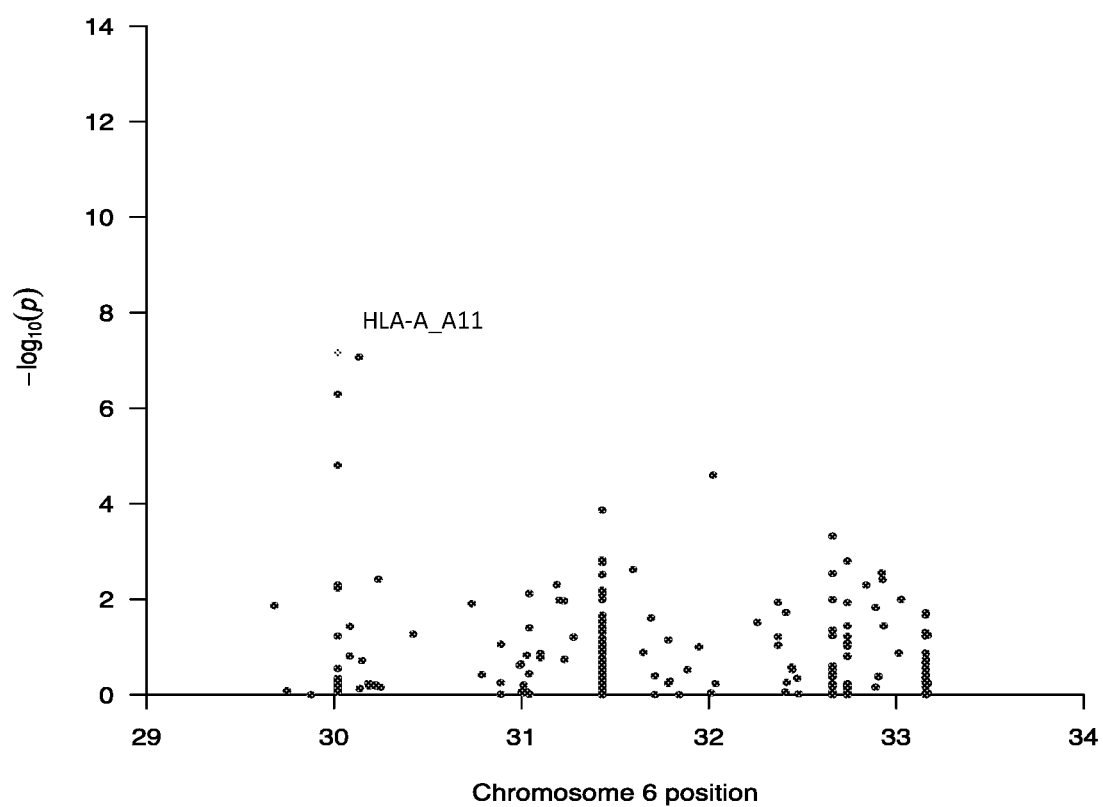

Recently, several studies have used genetic information derived from diabetes-associated risk variants across the genome to reclassify diabetes [6]. To date, comprehensive genetic studies of T1D and T2D have uncovered dozens of distinct susceptibility loci for each of these two diseases [7-9]. Initial analyses of T1D loci in relatively small LADA cohorts have consistently shown an association with the T1D locus HLA-DQB1, which resides in the major histocompatibility complex (MHC) [3, 10, 11], as well as at PTPN22 and INS [12, 13]. Similar analyses of T2D loci have suggested an association in LADA with the strongest T2D locus harboring TCF7L2 [12, 14, 15] and the ZMIZ1 locus [16]. A significant challenge of these studies has been the lack of statistical power due to the small number of LADA patients included. Thus, the genetic etiology of LADA remains largely unresolved.

To quantify the genetic liability to LADA contributed by genetic risk factors for T1D and T2D, we amassed the largest LADA cohort to date. By assessing the association of these variants in LADA, we have identified a biomarker which differentiates LADA from T1D.

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such that which causes sickle cell are responsible for disease. Other SNPs are normal variations in the genome. Haplotypes of interest can be identified utilizing SNPs as a flag for such haplotypes.

The phrase "Type 1 diabetes (T1D)" refers to a chronic (lifelong) disease that occurs when the pancreas produces too little insulin to regulate blood sugar levels appropriately. T1D, often called juvenile or insulin-dependent diabetes results from altered metabolism of carbohydrates (including sugars such as glucose), proteins, and fats. In type 1 diabetes, the beta cells of the pancreas produce little or no insulin, the hormone that allows glucose to enter body cells. Once glucose enters a cell, it is used as fuel. Without adequate insulin, glucose builds up in the bloodstream instead of going into the cells. The body is unable to use this glucose for energy despite high levels in the bloodstream, leading to increased hunger. In addition, the high levels of glucose in the blood cause the patient to urinate more, which in turn causes excessive thirst. Within 5 to 10 years after diagnosis, the insulin-producing beta cells of the pancreas are completely destroyed, and no more insulin is produced.

"T1D-associated SNP or specific marker" is a SNP or marker which is associated with an increased or decreased risk of developing TID not found normal patients who do not have this disease. Such markers may include but are not limited to nucleic acids, proteins encoded thereby, or other small molecules. Type 1 diabetes can occur at any age, but it usually starts in people younger than 30. Symptoms are usually severe and occur rapidly. The exact cause of type 1 diabetes is not known. Type 1 diabetes accounts for 3% of all new cases of diabetes each year. There is 1 new case per every 7,000 children per year.

Latent autoimmune diabetes of adults (LADA) is a form of diabetes mellitus type 1 that occurs in adulthood, often with a slower course of onset than type 1 diabetes diagnosed in juveniles. [3] LADA is often referred to as diabetes type 1.5. Adults with LADA may initially be diagnosed incorrectly as having type 2 diabetes based on their age, particularly if they have risk factors for type 2 diabetes such as a strong family history or obesity. The diagnosis is typically based on the finding of hyperglycemia together with the clinical impression that islet failure rather than insulin resistance is the main cause; detection of a low C-peptide and raised antibodies against the islets of Langerhans support the diagnosis. LADA is typically treated with the usual oral treatments for type 2 diabetes for a certain period of time, after which insulin treatment is usually necessary, as well as long-term monitoring for complications.

LADA-associated SNP or specific marker" is a SNP or marker which is associated with an increased or decreased risk of developing LADA not found normal patients who do not have this disease. Such markers may include but are not limited to nucleic acids, proteins encoded thereby, or other small molecules.

The Major Histocompatibility Complex (MHC) spans 4 megabases (Mb) and contains 149 genes, of which eight (the class II loci HLA-DRB1, HLA-DQB1, HLA-DQA1, HLA-DPB1, HLA-DPA1; the class I loci HLA-A, HLA-B and HLA-C) are the highly polymorphic immune response genes.

A "haplotype" as used herein refers to a set of DNA variations, or polymorphisms, that tend to be inherited together. A haplotype can refer to a combination of alleles or to a set of single nucleotide polymorphisms (SNPs) found on the same chromosome. "Haplotype" is derived from the word "haploid," which describes cells with only one set of chromosomes, and from the word "genotype," which refers to the genetic makeup of an organism. A haplotype can describe a pair of genes inherited together from one parent on one chromosome, or it can describe all of the genes on a chromosome that were inherited together from a single parent. This group of genes was inherited together because of genetic linkage, or the phenomenon by which genes that are close to each other on the same chromosome are often inherited together. In addition, the term "haplotype" can also refer to the inheritance of a cluster of single nucleotide polymorphisms (SNPs), which are variations at single positions in the DNA sequence among individuals. By examining haplotypes, scientists can identify patterns of genetic variation that are associated with health and disease states. For instance, if a haplotype is associated with a certain disease, then scientists can examine stretches of DNA near the SNP cluster to try to identify the gene or genes responsible for causing the disease.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose. "Sample" or "patient sample" or "biological sample" generally refers to a sample which may be tested for a particular molecule, preferably an T1D or LADA specific marker molecule, such as a marker shown in the tables provided below. Samples may include but are not limited to cells, body fluids, including blood, serum, plasma, urine, saliva, tears, pleural fluid and the like.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with T1D or LADA. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated. Thus, the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus, if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any T1D or LADA specific marker gene or nucleic acid, but does not hybridize to other human nucleotides. Also, polynucleotide which "specifically hybridizes" may hybridize only to a T1D or LADA specific marker. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m=81.5° \text{ C.}+16.6 \text{ Log[Na+]}+0.41(\% \ G+C)-0.63(\% \text{ formamide})-600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide" or "oligo" as used herein means a short sequence of DNA or DNA derivatives typically 8 to 35 nucleotides in length, primers, or probes. An oligonucleotide can be derived synthetically, by cloning or by amplification. An oligo is defined as a nucleic acid molecule comprised of two or more ribo- or deoxyribonucleotides, preferably more than three. The exact size of the oligonucleotide will depend on various factors and on the particular application and use of the oligonucleotide. The term "derivative" is intended to include any of the above described variants when comprising an additional chemical moiety not normally a part of these molecules. These chemical moieties can have varying purposes including, improving solubility, absorption, biological half life, decreasing toxicity and eliminating or decreasing undesirable side effects. Oligos can serve as probes or primers to identify nucleic acid sequences of interest.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 10-15, 15-25, 25-50 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, CA, USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, peptide-tethering, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the T1D or LADA specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the T1D specific marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long. "Sample" or "patient sample" or "biological sample" generally refers to a sample which may be tested for a particular molecule, preferably a T1D or LADA specific marker molecule. Samples may include but are not limited to cells, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, small molecules, antibodies, peptides, peptide/DNA complexes, and any nucleic acid based molecule, for example an oligo, which exhibits the capacity to modulate the activity of the SNP containing nucleic acids described herein or their encoded proteins. Agents are evaluated for potential biological activity by inclusion in screening assays described herein below.

The term "modulate" as used herein refers increasing or decreasing. For example, the term modulate refers to the ability of a compound or test agent to interfere with signaling or activity of a gene or protein of the present invention. This includes altering the activity of natural killer cells, and preventing autoimmune beta cell destruction.

As used herein, "treating" a condition or patient refers to taking steps to obtain beneficial or desired results, including clinical results. For purposes of this invention, beneficial or desired clinical results include, but are not limited to, alleviation or amelioration of one or more symptoms of diabetes, diminishment of extent of disease, delay, slowing, or prevention of disease progression, amelioration, palliation or stabilization of the disease state, and other beneficial results described below. Symptoms of diabetes include low or inadequate levels of insulin or insulin activity, frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, excessive or unusual infections, hyperglycemia, loss of glycemic control, fluctuations in postprandial blood glucose, fluctuations in blood glucagon, fluctuations in blood triglycerides. Diabetes may be diagnosed by methods well known to one of ordinary skill in the art. For example, commonly, diabetics have a plasma blood glucose result of greater than 126 mg/dL of glucose. Pre-diabetes, which may also be treated by the compositions and methods of the invention is commonly diagnosed in patients with a blood glucose result between 100 and 125 mg/dL of glucose. Other symptoms may also be used to diagnose diabetes, related diseases and conditions, and diseases and conditions affected by diminished pancreatic function.

As used herein, "reduction" of a symptom or symptoms (and grammatical equivalents of this phrase) means decreasing of the severity or frequency of the symptom(s), or elimination of the symptom(s).

As used herein, "impaired glucose homeostasis" is a diminished capacity in a subject for regulating glucose by a system of feedback controls, so as to stabilize health and functioning. Conditions that are associated with or are a risk factor for impaired glucose homeostasis include new onset type 1 and 2 diabetes, previously existing type 1 and 2 diabetes, latent autoimmune diabetes of adulthood (LADA), glutamic acid decarboxylase-65 autoimmunity, prediabetes, metabolic syndrome. hyperglycemia, glucose intolerance, beta cell impairment or deficiency, insulin resistance, obesity, polycystic ovarian syndrome, nonalcoholic steatohepatitis, hyperlipidemia, and hypertriglyceridemia.

As used herein, "administering" or "administration of" a drug to a subject (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

As used herein, a "subject" or "patient" is a mammal, typically a human, but optionally a mammalian animal of veterinary importance, including but not limited to horses, cattle, sheep, dogs, and cats. "Patient" and "subject" may be used interchangeably herein.

As used herein, a "therapeutically effective amount" of a drug or agent is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

As used herein, a "therapeutically effective amount" of a drug may also be an amount of a drug that when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose and may occur only after administration of a series of doses. Thus, a therapeutically effective amount may be administered in one or more administrations.

Kits and Articles of Manufacture

The present invention provides a kit which may contain an T1D and LADA specific marker polynucleotides or one or more such markers immobilized (covalently bonded or otherwise affixed) on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof. The kit may also comprise reagents suitable for detection of autoimmune antibodies associated with the diabetic phenotype. An exemplary kit comprises a set of probes or primers of sufficient length and composition to detect nucleic acids encoding MHC haplotypes consisting of HLA-DQB1*0302, HLA-DQB1*0201, HLA-DRB1*1501, HLA-B*3906 and HLA-A*11, said probes or primers being covalently affixed to a solid support, reagents suitable for polymerase chain reaction, reagents for detecting hybridization of nucleic acids isolated from said biological sample to said solid support, detectably labeled antibodies for detection of one or more autoantibody selected from Glutamic acid decarboxylase autoantibodies (GADA), Islet cell autoantibodies (ICA), IA-2-protein tyrosine phosphatase-like protein autoantibodies (IA-2A), Insulin autoantibodies (IAA), Zinc transporter (ZnT8) autoantibodies and regents for detecting immunocomplex formation between said detectably labeled antibody and said autoantibody.

Pharmaceuticals and Peptide Therapies

The elucidation of the role played by the T1D associated vs LADA associated haplotypes described herein in cellular metabolism facilitates the development of pharmaceutical compositions useful for treatment and diagnosis of T1D and LADA. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

As it is presently understood, RNA interference involves a multi-step process. Double stranded RNAs are cleaved by the endonuclease Dicer to generate nucleotide fragments (siRNA). The siRNA duplex is resolved into 2 single stranded RNAs, one strand being incorporated into a protein-containing complex where it functions as guide RNA to direct cleavage of the target RNA (Schwarz et al, Mol. Cell. 10:537 548 (2002), Zamore et al, Cell 101:25 33 (2000)), thus silencing a specific genetic message (see also Zeng et al, Proc. Natl. Acad. Sci. 100:9779 (2003)).

The invention includes a method of treating T1D or LADA in a mammal. Preferably, the mammal is a human, and the term "patient" as used herein refers to a human.

Pharmaceutical compositions that are useful in the methods of the invention may be administered systemically in parenteral, oral solid and liquid formulations, ophthalmic, suppository, aerosol, topical or other similar formulations. In addition to the appropriate insulin or insulin regulating compound, these pharmaceutical compositions may contain pharmaceutically-acceptable carriers and other ingredients known to enhance and facilitate drug administration. Thus, such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate compound to a patient according to the methods of the invention.

The materials and methods set forth below are provided to facilitate the practice of the present invention.

Study Population:

978 LADA cases were obtained from two European cohorts. A description of the participants and study design has been published elsewhere (Hawa, M. I., et al., Adult-onset autoimmune diabetes in Europe is prevalent with a broad clinical phenotype: Action LADA 7. Diabetes Care, 2013. 36(4): p. 908-13). The criteria for LADA diagnosis was more stringent to avoid potential false positives. All participants were diagnosed with LADA if they were aged 30-70 years, tested positive for diabetes-associated Glutamic Acid Decarboxylase autoantibodies (GADA), and were not given insulin treatment for at least 6 months after diagnosis. Samples were tested for serum autoantibodies to GADA and insulinoma associated antigen-2 (IA2A). The population-based controls comprised 1,057 non-diabetic healthy, normally developing children of European ancestry. We leveraged the cohorts which were used in identifying the HLA-B signal in the Wellcome Trust Case Control Consortium (WTCCC) data, which was reported by Nejentsev, S., et al. (Localization of type 1 diabetes susceptibility to the MHC class I genes HLA-B and HLA-A. Nature, 2007. 450(7171): p. 887-92; incorporated herein by reference) in order to replicate and with what had been previously reported for that cohort. This consisted of 2,820 healthy adult British Birth cohort controls and 2,000 individuals with childhood-onset T1D from the WTCCC (Genome-wide association study of 14,000 cases of seven common diseases and 3,000 shared controls. Nature, 2007. 447(7145): p. 661-78). Individual data from WTCCC is available through the Consortium's Data access committee on the world wide web at wtcc-c.org.uk.

HLA Imputation:

Starting from the genotyped SNPs, we imputed chromosome 6 which harbors the classical HLA alleles and corresponding polymorphic amino acids within classical HLA proteins using the HLA imputation software SNP2HLA as described previously (Jia, X., et al., Imputing amino acid polymorphisms in human leukocyte antigens. PLoS One, 2013. 8(6): p. e64683; incorporated by reference herein). The HLA alleles of the LADA cases (n=978) and WTCCC T1D cases (n=1,990) were all imputed to the 4-digit resolution. In total, 8,972 variants including SNPs, amino acids and classical HLA alleles at 2- and 4-digit resolution were imputed. Removing HLA alleles that have a frequency of less than 1%, were removed. 474 HLA alleles and 1276 amino acids markers were tested separately for association in the MEW region.

Association Test:

Logistic regression using SNPTEST (Marchini, J., et al., A new multipoint method for genome-wide association studies by imputation of genotypes. Nat Genet, 2007. 39(7): p. 906-13; incorporated by reference herein), was applied for testing for association, including the first 4 principal components as covariates to account for population stratification. Conditional analyses were performed by using a forward stepwise conditional logistic regression selection by added the most significant allele association, and repeated until we were able to replicate observation of the HLA-B signal in WTCCC data, which was reported by Todd et al (Nejentsev, S., et al., Localization of type 1 diabetes susceptibility to the MHC class I genes HLA-B and HLA-A. Nature, 2007. 450(7171): p. 887-92). The same model was tested in the LADA cohort, where HLA-DQB1*0302, HLA-DQB1*0201, HLA-DRB1*1501 were conditioned on. A chi-square test was used to test the null hypothesis that the role of these T1D associated HLA alleles behave the same in LADA. We further tested and compared the association in a random sample of 978 T1D cases and 1,057 controls, as well as a random sample of 489 cases and 1,057 controls, to rule out concern over power issues.

Individual Candidate SNP Association Tests:

To investigate the role of previously discovered T1D and T2D variants in LADA, we tested 67 T1D SNPs (from Immunobase on the world wide web at immunobase.org, and 71 T2D SNPs (from the T2D study led by the DIAbetes Genetics Replication And Meta-analysis (DIAGRAM) Consortium. Association between each SNP and case/control status was assessed using a univariate linear mixed model within GEMMA (Zhou X, Stephens M: Genome-wide efficient mixed-model analysis for association studies. *Nat Genet* 2012, 44(7):821-824). This model accounts for population stratification and relatedness using the Wald test and the restricted maximum likelihood estimate of β. We tested each SNP in LADA cases versus controls and in LADA cases versus T1D or T2D cases. Significant associations were called after Bonferroni correction for multiple testing. Analysis was performed for all LADA cases (n=978), LADA cases positive for GADA only (n=669), and LADA cases positive for both GADA and IA2A (n=309). Approximated odds ratios were calculated using μ (intercept) and β (effect size) estimates from the linear mixed model, with the formula: $OR=e^{\beta/\mu(1-\mu)}$.

The following examples are provided to illustrate certain embodiments of the invention. They are not intended to limit the invention in any way.

Example I

Conditioning on MHC Class II Genes, HLA-DQB1 and HLA-DRB1 Distinguishes T1D Patients from LADA Patients Latent autoimmune diabetes in adults (LADA), also known as "Type 1.5 diabetes", is the most prevalent form of autoimmune diabetes, sharing features with both type 1 diabetes (T1D) and type 2 diabetes (T2D). Similar to T2D, those with LADA present in adulthood initially insulin independent for at least six months and are positive for T1D-associated autoantibodies. LADA is regularly misclassified as T2D, often leading to suboptimal treatments for those patients. Recently, we have shown that despite being clinically similar to T2D, LADA is genetically closer to T1D (Mishra et al., 2017).

However, to further understand how LADA differs genetically from T1D, we explored the genetic sequence of the major histocompatibility complex (MHC), which is a highly variable region harboring a variant very highly significantly associated with both T1D and LADA. MHC class II genes have known to be associated T1D, however there was limited evidence of MHC class I genes associated with the disease. Indeed, the major histocompatibility complex (MHC) on chromosome 6 is associated with susceptibility to more common diseases than any other region of the human genome, including almost all disorders classified as autoimmune. In type 1 diabetes the major genetic susceptibility determinants have been mapped to the MHC class II genes HLA-DQB1 and HLA-DRB1. Significantly associated signals in the HLA-B and HLA-A gene have been observed independent of these top T1D-associated class II genes (Nejentsev et al., 2007). The HLA-DQB1 and HLA-DRB1 genes are also associated with LADA, though with a much weaker signal compared to T1D.

We performed a conditional analysis on both T1D cases and controls as well as LADA cases and controls and were able to recapitulate the finding of HLA-B and HLA-A T1D association, however we did not observe this association in LADA cases, in fact the HLA-B signal becomes weaker in LADA when conditioning on MHC class II genes. See FIG. 1. This finding not only provides a greater understanding the molecular mechanisms underlying diabetes, but also provides a biomarker that distinguishes LADA from T1D. Identification of this biomarker provides new therapeutic approaches and should lead to new reagents for efficient diagnosis and treatment autoimmune disease. Indeed, this key signature can be used to identify those individuals who will present with the disease in childhood as well as those who will need yearly monitoring for diabetic markers and symptoms which present in adulthood.

The conditional analysis was repeated to test imputed amino acid polymorphisms for the classic HLA alleles to gain further evidence to support these distinguishing genetic signatures. The role of amino acid position 57 in HLA-DQB1 is known to be associated with T1D, which we were able to recapitulate in the T1D dataset. Conditioning on this amino acid position in HLA-DQB1, along with amino acid position 11 and position 86 in HLA-DRB1, there was an independently strong association signal in amino acid position 114 in HLA-A. Subsequently, conditioning on HLA-DQB1, HLA-DRB1, and HLA-A, there was a significant association of amino acid position 158 in HLA-B. Although, we observed a significant association of amino position 71 in HLA-DRB1, amino acid position 57 in HLA-DQB1 and amino acid position 185 in HLA-DQB1, we did not observe significant association HLA-A or HLA-B in LADA cases, further supporting MHC class I markers as key discriminators for LADA and T1D. After sensitivity analyses through the systematic decreasing of the sample size of T1D and WTCCC controls in order to contrast with the LADA vs controls sample size, the independent effects of HLA-B and HLA-A consistently remained (both at the single nucleotide and amino acid level).

Example II

Methods for Testing and Treating and/or Testing and Monitoring a Subject for the Development of LADA Distinguishing LADA from both T1D and T2D is important to ensure that the subject is treated properly. Indeed, misclassifying a LADA subject as a T2D subject can result in insufficient glycemic control and harm to patients. In such cases, clinicians will have difficulty in titrating the diabetic oral treatment medications (e.g., metformin and glyburide), and, because they are ineffective, will suspect non-adherence and attempt to enforce further life style changes. LADA patients often require insulin within 5 years of diagnosis, and other therapy options that preserve beta cell function, including dipeptidyl peptidase-4 inhibitors, glucagon-like peptide 1 receptor agonists and thiazolidinediones should be considered. Notably, therapy options such as sulfonylureas that increase the rate of deterioration of C-peptide secretion, further depleting insulin levels, should be avoided.

In order to identify an individual at an increased risk for LADA, or to alleviate a sign or symptom of the disease, a test and treat protocol is provided herein.

First, a biological sample, and/or genotyping information is obtained from a patient. Genetic information gleaned from nucleic acids present in the sample would then be assessed for the presence or absence of the LADA biomarker for example. As discussed above, absence of the HLA-B allele is indicative of an increased risk of LADA, rather than T1D. Identifying the presence of this haplotype, provides the clinician with guidance as to whether monitoring the patient for the development of LADA or immediate treatment is necessary. In cases where the patient has tested positive for LADA but does not yet show signs of the disease, the patient can be periodically monitored for the development of autoantibodies, including but not limited to Glutamic acid decarboxylase autoantibodies (GADA), Islet cell autoantibodies (ICA) IA-2-protein tyrosine phosphatase-like protein autoantibodies (IA-2A), Insulin autoantibodies (IAA), and Zinc transporter (ZnT8) autoantibodies. Patients can also be monitored for insulin, glucagon and blood sugar levels as well.

One skilled in the art would know that the amount of anti-diabetes agent described above required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having LADA.

The effective dose of LADA therapeutic agent(s) will depend on the mode of administration, and the weight of the individual being treated. The dosages described herein are generally those for an average adult but can be adjusted for the treatment of children. The dose will generally range from about 0.001 mg to about 1000 mg.

In an individual suffering from LADA, in particular a more severe form of the disease, administration of anti-diabetic therapeutic agents can be particularly useful when administered in combination, for example, with a conventional agent for treating such a disease. The skilled artisan would administer the therapeutic agent(s), alone or in combination and would monitor the effectiveness of such treatment using routine methods such as kidney function tests, blood sugar assays, or, where indicated, histopathologic methods.

Administration of the pharmaceutical preparation is preferably in an "effective amount" this being sufficient to show benefit to the individual. This amount prevents, alleviates, abates, or otherwise reduces the severity of diabetes symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

REFERENCES

1. Maddaloni E, Lessan N, Al Tikriti A, Buzzetti R, Pozzilli P, Barakat M T: Latent Autoimmune Diabetes in Adults in the United Arab Emirates: Clinical Features and Factors Related to Insulin-Requirement. PLoS One 2015, 10(8): e0131837.
2. Hawa M I, Kolb H, Schloot N, Beyan H, Paschou S A, Buzzetti R, Mauricio D, De Leiva A, Yderstraede K, Beck-Neilsen H et al: Adult-onset autoimmune diabetes in Europe is prevalent with a broad clinical phenotype: Action LADA 7. Diabetes Care 2013, 36(4):908-913.
3. Tuomi T, Carlsson A, Li H, Isomaa B, Miettinen A, Nilsson A, Nissen M, Ehrnstrom B O, Forsen B, Snickars B et al: Clinical and genetic characteristics of type 2 diabetes with and without GAD antibodies. Diabetes 1999, 48(1):150-157.
4. Zhou Z, Xiang Y, Ji L, Jia W, Ning G, Huang G, Yang L, Lin J, Liu Z, Hagopian W A et al: Frequency, immunogenetics, and clinical characteristics of latent autoimmune diabetes in China (LADA China study): a nationwide, multicenter, clinic-based cross-sectional study. Diabetes 2013, 62(2):543-550.
5. Tuomi T, Groop L C, Zimmet P Z, Rowley M J, Knowles W, Mackay I R: Antibodies to glutamic acid decarboxylase reveal latent autoimmune diabetes mellitus in adults with a non-insulin-dependent onset of disease. Diabetes 1993, 42(2):359-362.
6. Oram R A, Patel K, Hill A, Shields B, McDonald T J, Jones A, Hattersley A T, Weedon M N: A Type 1 Diabetes Genetic Risk Score Can Aid Discrimination Between Type 1 and Type 2 Diabetes in Young Adults. Diabetes Care 2016, 39(3):337-344.
7. Bradfield J P, Qu H Q, Wang K, Zhang H, Sleiman P M, Kim C E, Mentch F D, Qiu H, Glessner J T, Thomas K A et al: A genome-wide meta-analysis of six type 1 diabetes cohorts identifies multiple associated loci. PLoS Genet 2011, 7(9):e1002293.
8. Wellcome Trust Case Control C: Genome-wide association study of 14,000 cases of seven common diseases and 3,000 shared controls. Nature 2007, 447(7145):661-678.
9. Consortium DIAGRM-a, Consortium AGENTD, Consortium SATD, Consortium MATD, Consortium TDGEbN-gsim-ES, Mahajan A, Go M J, Zhang W, Below J E, Gaulton K J et al: Genome-wide trans-ancestry meta-analysis provides insight into the genetic architecture of type 2 diabetes susceptibility. Nature genetics 2014, 46(3):234-244.
10. Desai M, Zeggini E, Horton V A, Owen K R, Hattersley A T, Levy J C, Walker M, Gillespie K M, Bingley P J, Hitman G A et al: An association analysis of the HLA gene region in latent autoimmune diabetes in adults. Diabetologia 2007, 50(1):68-73.
11. Horton V, Stratton I, Bottazzo G F, Shattock M, Mackay I, Zimmet P, Manley S, Holman R, Turner R: Genetic heterogeneity of autoimmune diabetes: age of presentation in adults is influenced by HLA DRB1 and DQB1 genotypes (UKPDS 43). UK Prospective Diabetes Study (UKPDS) Group. Diabetologia 1999, 42(5):608-616.
12. Cervin C, Lyssenko V, Bakhtadze E, Lindholm E, Nilsson P, Tuomi T, Cilio C M, Groop L: Genetic similarities between latent autoimmune diabetes in adults, type 1 diabetes, and type 2 diabetes. Diabetes 2008, 57(5):1433-1437.
13. Desai M, Zeggini E, Horton V A, Owen K R, Hattersley A T, Levy J C, Hitman G A, Walker M, Holman R R, McCarthy M I et al: The variable number of tandem repeats upstream of the insulin gene is a susceptibility locus for latent autoimmune diabetes in adults. Diabetes 2006, 55(6):1890-1894.
14. Lukacs K, Hosszufalusi N, Dinya E, Bakacs M, Madacsy L, Panczel P: The type 2 diabetes-associated variant in TCF7L2 is associated with latent autoimmune diabetes in adult Europeans and the gene effect is modified by obesity: a meta-analysis and an individual study. Diabetologia 2012, 55(3):689-693.
15. Zampetti S, Spoletini M, Petrone A, Capizzi M, Arpi M L, Tiberti C, Di Pietro S, Bosi E, Pozzilli P, Giorgino F et al: Association of TCF7L2 gene variants with low GAD autoantibody titre in LADA subjects (NIRAD Study 5). Diabet Med 2010, 27(6):701-704.
16. Andersen M K, Sterner M, Forsen T, Karajamaki A, Rolandsson O, Forsblom C, Groop P H, Lahti K, Nilsson P M, Groop L et al: Type 2 diabetes susceptibility gene variants predispose to adult-onset autoimmune diabetes. Diabetologia 2014, 57(9):1859-1868.

17. Todd J A, Bell J I, McDevitt H O (1987) HLA-DQ beta gene contributes to susceptibility and resistance to insulin-dependent diabetes mellitus. Nature 329: 599-604.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. A method for treating a subject with an altered risk of Latent autoimmune diabetes (LADA) over Type 1 Diabetes (T1D), the method comprising;
   a) providing a biological sample comprising nucleic acids obtained from a subject having diabetic symptoms;
   b) genotyping said sample for MHC HLA haplotypes HLA-DQB1*0302, HLA-DQB1*0201, HLA-DRB1*1501, HLA-B*3906 and HLA-A*11;
   c) identifying from said genotyping that the said subject lacks HLA-B*3906 and HLA-A*11 biomarkers, absence of said HLA-B*3906 and HLA-A*11 being indicative of an increased risk of LADA over T1D; and
   d) after steps b) and c), treating the subject with an agent which modulates LADA symptoms.

2. The method of claim 1, further comprising monitoring the subject by
   a) obtaining at least one additional blood sample from said subject; and
   b) detecting in said at least one additional sample one or more autoimmune disease and/or diabetes biomarkers.

3. The method of claim 1, wherein said subject has not been previously diagnosed with either T1D or LADA.

4. The method of claim 1, further comprising detecting in said sample one or more autoimmune disease biomarkers, wherein said autoimmune biomarker is one or more autoantibody selected from Glutamic acid decarboxylase autoantibodies (GADA), Islet cell autoantibodies (ICA), IA-2-protein tyrosine phosphatase-like protein autoantibodies (IA-2A), Insulin autoantibodies (IAA), Zinc transporter (ZnT8) autoantibodies.

5. The method of claim 1, wherein levels of one or more of insulin, glucagon and blood sugar are monitored in said subject.

6. The method of claim 1, wherein the haplotypes HLA-DQB1*0302, HLA-DQB1*0201, HLA-DRB1*1501 are present in said sample.

* * * * *

SEQUENCE LISTING

```
<160> NUMBER OF SEQ ID NOS: 5

<210> SEQ ID NO 1
<211> LENGTH: 786
<212> TYPE: DNA
<213> ORGANISM: Homo sapiens

<400> SEQUENCE: 1
atgtcttgga aaaaggcttt gcggatcccc ggaggccttc gggcagcaac tgtgaccttg      60
atgctgtcga tgctgagcac cccagtggct gagggcagag actctcccga ggatttcgtg     120
taccagttta agggcatgtg ctacttcacc aacgggacag agcgcgtgcg tcttgtgagc     180
agaagcatct ataaccgaga agagatcgtg cgcttcgaca gcgacgtggg ggagttccgg     240
gcggtgacgc tgctggggct gcctgccgcc gagtactgga cagccagaa ggacatcctg      300 gagaggaaac gggcggcggt ggacagggtg tgcagacaca actaccagtt ggagctccgc     360
acgaccttgc agcggcgagt ggagcccaca gtgaccatct ccccatccag gacagaggcc     420
ctcaaccacc acaacctgct ggtctgctcg gtgacagatt tctatccagc ccagatcaaa     480
gtccggtggt ttcggaatga ccaggaggag acagctggcg ttgtgtccac ccccttatt     540 aggaatggtg actggacctt ccagatcctg gtgatgctgg aaatgactcc ccagcgtgga     600
gacgtctaca cctgccacgt ggagcacccc agcctccaga gccccatcac cgtggagtgg     660
cgggctcaat ctgaatctgc ccagagcaag atgctgagtg gcattggagg cttcgtgctg     720
gggctgatct tcctcgggct gggccttatc atccatcaca ggagtcagaa agggctcctg     780
cactga                                                                786

<210> SEQ ID NO 2
<211> LENGTH: 786
<212> TYPE: DNA
<213> ORGANISM: Homo sapiens

<400> SEQUENCE: 2
atgtcttgga agaaggcttt gcggatccct ggaggccttc gggtagcaac tgtgaccttg      60
atgctggcga tgctgagcac cccggtggct gagggcagag actctcccga ggatttcgtg     120
taccagttta agggcatgtg ctacttcacc aacgggacgg agcgcgtgcg tcttgtgacc     180
agatacatct ataaccgaga ggagtacgca cgcttcgaca gcgacgtggg ggtgtatcgg     240
gcggtgacgc cgctggggcc gcctgccgcc gagtactgga cagccagaa ggaagtcctg      300 gagaggaccc gggcggagtt ggacacggtg tgcagacaca actaccagtt ggagctccgc     360
acgaccttgc agcggcgagt ggagcccaca gtgaccatct ccccatccag gacagaggcc     420
ctcaaccacc acaacctgct ggtctgctca gtgacagatt tctatccagc ccagatcaaa     480
gtccggtggt ttcggaatga ccaggaggag acaactggcg ttgtgtccac ccccttatt     540 aggaacggtg actggacctt ccagatcctg gtgatgctgg aaatgactcc ccagcgtgga     600
gacgtctaca cctgccacgt ggagcacccc agcctccaga ccccatcat cgtggagtgg     660
```

```
cgggctcagt ctgaatctgc ccagagcaag atgctgagtg gcattggagg cttcgtgctg      720
gggctgatct tcctcgggct gggccttatt atccatcaca ggagtcagaa agggctcctg      780
cactga                                                                 786
```

```
<210> SEQ ID NO 3
<211> LENGTH: 801
<212> TYPE: DNA
<213> ORGANISM: Homo sapiens

<400> SEQUENCE: 3
atggtgtgtc tgaagctccc tggaggctcc tgcatgacag cgctgacagt gacactgatg       60
gtgctgagct ccccactggc tttgtctggg acacccgac cacgtttcct gtggcagcct       120
aagagggagt gtcatttctt caatgggacg gagcgggtgc ggttcctgga cagatacttc      180
tataaccagg aggagtccgt gcgcttcgac agcgacgtgg gggagttccg gcggtgacg       240 gagctggggc ggcctgacgc tgagtactgg aacagccaga aggacatcct ggagcaggcg      300
cgggccgcgg tggacaccta ctgcagacac aactacgggg ttgtggagag cttcacagtg      360
cagcggcgag tccaacctaa ggtgactgta tatccttcaa agacccagcc cctgcagcac      420
cacaacctcc tggtctgctc tgtgagtggt ttctatccag gcagcattga agtcaggtgg      480
ttcctgaacg gccaggaaga aaggctggga tggtgtccca caggcctgat ccagaatgga      540
gactggacct tccagaccct ggtgatgctg gaaacagttc ctcgaagtgg agaggtttac      600
acctgccaag tggagcaccc aagcgtgaca agccctctca cagtggaatg gagagcacgg      660
tctgaatctg cacagagcaa gatgctgagt ggagtcgggg gctttgtgct gggcctgctc      720
ttccttgggg ccgggctgtt catctacttc aggaatcaga aggacactc tggacttcag       780 ccaacaggat tcctgagctg a                                                801
```

```
<210> SEQ ID NO 4
<211> LENGTH: 1089
<212> TYPE: DNA
<213> ORGANISM: Homo sapiens

<400> SEQUENCE: 4
atgctggtca tggcgccccg aaccgtcctc ctgctgctct cggcggccct ggccctgacc       60
gagacctggg ccggctccca ctccatgagg tatttctaca cctccgtgtc ccggcccggc      120
cgcggggagc cccgcttcat ctcagtgggc tacgtggacg acacgcagtt cgtgaggttc      180 acagcgacg ccgcgagtcc gagagaggag ccgcgggcgc cgtggataga gcaggagggg      240
ccggaatatt gggaccggaa cacacagatc tgcaagacca acacacagac tgaccgagag      300
agcctgcgga acctgcgcgg ctactacaac cagagcgagg ccgggtctca cacttggcag      360
acgatgtacg gctgcgacgt ggggccggac gggcgcctcc tccgcgggca taaccagttc      420
gcctacgacg gcaaggatta catcgccctg aacgaggacc tgagctcctg gaccgcggcg      480
gacaccgcgg ctcagatcac ccagcgcaag tgggaggcgg cccgtgtggc ggagcagctg      540
agaacctacc tggagggcac gtgcgtggag tggctccgca gatacctgga gaacgggaag      600
gagacgctgc agcgcgcgga cccccaaag acacatgtga cccaccaccc catctctgac      660
catgaggcca ccctgaggtg ctgggccctg ggcttctacc ctgcggagat cacactgacc      720
tggcagcggg atggcgagga ccaaactcag gacaccgagc ttgtggagac cagaccagca      780
ggagacagaa ccttccagaa gtgggcagct gtggtggtgc cttctggaga agagcagaga      840
tacacatgcc atgtacagca tgaggggctg ccgaagcccc tcaccctgag atgggagcca      900
```

```
tcttcccagt ccaccgtccc catcgtgggc attgttgctg gcctggctgt cctagcagtt      960
gtggtcatcg gagctgtggt cgctgctgtg atgtgtagga ggaagagttc aggtggaaaa     1020
ggagggagct actctcaggc tgcgtccagc acagtgccc agggctctga tgtgtctctc      1080
acagcttga                                                             1089
```

<210> SEQ ID NO 5
<211> LENGTH: 1098
<212> TYPE: DNA
<213> ORGANISM: Homo sapiens

<400> SEQUENCE: 5

```
atggccgtca tggcgccccg aaccctcctc ctgctactct cggggcccct ggccctgacc       60
cagacctggg cgggctccca ctccatgagg tatttctaca cctccgtgtc ccggcccggc      120
cgcggggagc cccgcttcat cgccgtgggc tacgtggacg acacgcagtt cgtgcggttc      180
gacagcgacg ccgcgagcca gaggatggag ccgcgggcgc cgtggataga gcaggagggg      240
ccggagtatt gggaccagga gacacggaat gtgaaggccc agtcacagac tgaccgagtg      300
gacctgggga ccctgcgcgg ctactacaac cagagcgagg acggttctca caccatccag      360
ataatgtatg gctgcgacgt ggggccggac gggcgcttcc tccgcgggta ccggcaggac      420
gcctacgacg gcaaggatta tatcgccctg aacgaggacc tgcgctcttg gaccgcggcg      480
gacatggcag ctcagatcac caagcgcaag tgggaggcgg cccatgcggc ggagcagcag      540
agagcctacc tggagggccg gtgcgtggag tggctccgca gatacctgga gaacgggaag      600
gagacgctgc agcgcacgga ccccccaag acacatatga cccaccaccc catctctgac       660
catgaggcca ccctgaggtg ctgggccctg ggcttctacc ctgcggagat cacactgacc      720
tggcagcggg atggggagga ccagacccag gacacggagc tcgtggagac caggcctgca      780
ggggatggaa ccttccagaa gtgggcggct gtggtggtgc cttctggaga ggagcagaga      840
tacacctgcc atgtgcagca tgagggtctg cccaagcccc tcaccctgag atgggagctg      900
tcttcccagc ccaccatccc catcgtgggc atcattgctg gcctggttct ccttggagct      960
gtgatcactg gagctgtggt cgctgccgtg atgtggagga ggaagagctc agatagaaaa     1020
ggagggagtt acactcaggc tgcaagcagt gacagtgccc agggctctga tgtgtctctc     1080
acagcttgta aagtgtga                                                  1098
```